United States Patent
Rink et al.

(10) Patent No.: US 10,555,771 B2
(45) Date of Patent: Feb. 11, 2020

(54) LASER BEAM CONTROL AND DELIVERY SYSTEM

(75) Inventors: John L. Rink, San Francisco, CA (US); Anh Hoang, Alameda, CA (US)

(73) Assignee: Xintec Corporation aba Convergent Laser Technology, Alameda, CA (US)

( * ) Notice: Subject to any disclaimer, the term of this patent is extended or adjusted under 35 U.S.C. 154(b) by 1216 days.

(21) Appl. No.: 13/698,026

(22) PCT Filed: May 16, 2011

(86) PCT No.: PCT/US2011/036687
§ 371 (c)(1),
(2), (4) Date: Aug. 26, 2015

(87) PCT Pub. No.: WO2011/143663
PCT Pub. Date: Nov. 17, 2011

(65) Prior Publication Data
US 2017/0354465 A1    Dec. 14, 2017

Related U.S. Application Data

(60) Provisional application No. 61/395,523, filed on May 14, 2010, provisional application No. 61/395,562, filed on May 14, 2010.

(51) Int. Cl.
| | | |
|---|---|---|
| A61N 5/06 | (2006.01) | |
| A61B 18/20 | (2006.01) | |
| A61B 90/98 | (2016.01) | |
| A61B 17/00 | (2006.01) | |
| A61B 18/00 | (2006.01) | |
| A61B 34/00 | (2016.01) | |

(52) U.S. Cl.
CPC ............ *A61B 18/201* (2013.01); *A61B 90/98* (2016.02); *A61B 34/25* (2016.02); *A61B 2017/00084* (2013.01); *A61B 2018/00047* (2013.01); *A61B 2018/00642* (2013.01); *A61B 2018/00702* (2013.01); *A61B 2018/00714* (2013.01); *A61B 2018/00785* (2013.01); *A61B 2018/00791* (2013.01); *A61B 2018/207* (2013.01); *A61B 2018/2065* (2013.01)

(58) Field of Classification Search
CPC ....... A61B 18/201; A61B 90/98; A61B 18/22; A61B 34/25; A61B 2018/2247; A61B 2017/0084; A61B 2018/00047; A61B 2018/00642; A61B 2018/00702; A61B 2018/00714; A61B 2018/00785; A61B 2018/00791; A61B 2018/2025; A61B 2018/2065; A61B 2018/2017
USPC .......................................................... 606/16
See application file for complete search history.

(56) References Cited

U.S. PATENT DOCUMENTS

| | | | |
|---|---|---|---|
| 2005/0185190 A1* | 8/2005 | Law ........................ | G01J 1/26 356/484 |
| 2006/0079762 A1* | 4/2006 | Norris ................ | A61B 1/00172 600/427 |
| 2007/0104066 A1* | 5/2007 | Abranovich ........... | G11B 20/10 369/59.19 |

* cited by examiner

*Primary Examiner* — Aaron F Roane
(74) *Attorney, Agent, or Firm* — Tue Nguyen; patent2ip LLC (57) ABSTRACT

The present invention relates generally to surgical lasers and more specifically to a laser beam control and delivery system that accurately and efficiently directs a laser beam into an optical fiber. The laser beam control and delivery system also provides additional functions, including a connection for a fiber tip temperature control system and a tissue temperature sensing system. The present invention also relates to a surgical laser system that has a high efficiency thermoelectric cooling system.

10 Claims, 9 Drawing Sheets

LASER BEAM CONTROL AND DELIVERY SYSTEM

FIELD OF THE INVENTION

The present invention relates generally to surgical lasers and more specifically to a laser beam control and delivery system that accurately and efficiently directs a laser beam into an optical fiber. The laser beam control and delivery system also provides additional functions, including a connection for a fiber tip temperature control system and a tissue temperature sensing system. The present invention also relates to a surgical laser system that has a high efficiency thermoelectric cooling system.

BACKGROUND OF THE INVENTION

The present invention relates to surgical lasers of the type where the laser beam from a laser source is delivered to the surgical site through an optical fiber. The laser source may be a gas laser, a solid state laser or, advantageously, one or more laser diodes. Surgical laser systems that utilize laser diodes are described in U.S. Provisional Applications 61/068,165 filed on Mar. 4, 2008 and 61/137,157 filed on Jul. 28, 2008. These and all patents and patent applications referred to herein are incorporated by reference in their entirety.

DESCRIPTION OF THE INVENTION

Figure 1:
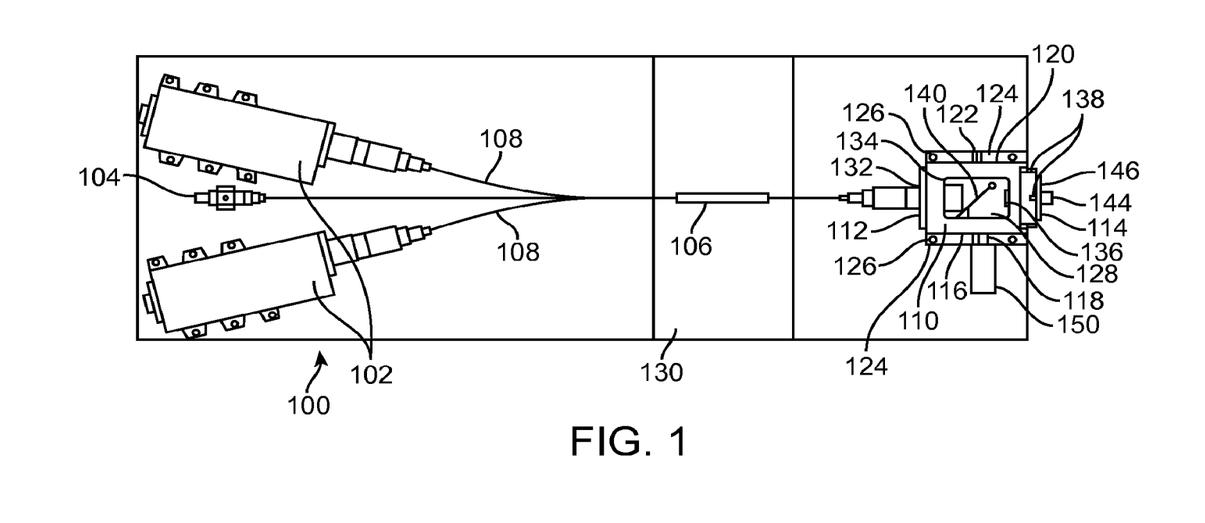
FIG. 1 shows a plan view of a surgical laser system utilizing two laser diodes and an aiming laser that are directed into an optical fiber using the laser beam control and delivery system of the present invention.
Figure 2:
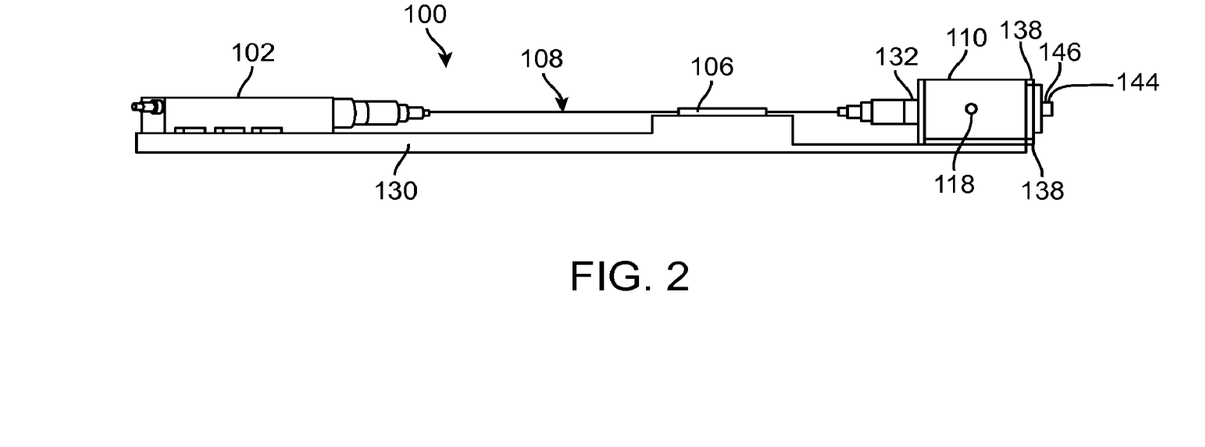
FIG. 2 shows a side view of the surgical laser system of FIG. 1.

FIG. 1 shows a plan view of a surgical laser system 100 utilizing the laser beam control and delivery system of the present invention. FIG. 2 shows a side view of the surgical laser system 100 of FIG. 1.

The surgical laser system 100 may utilize a laser source that comprises a gas laser, a solid state laser or, advantageously, one or more laser diodes 102. In the example shown, the laser system utilizes two fiber-coupled laser diodes 102 and an aiming laser 104. The output beams from the two laser diodes 102 and the aiming laser 104 are combined using a beam combiner 106. The beam combiner 106 is formed by fusing the cores of the optical fibers 108 from the two laser diodes 102 and the aiming laser 104 together to create a single fiber that combines the output beams from the three laser sources. Alternate embodiments may utilize multiple laser diode modules or arrays of laser diodes and one or more aiming lasers.

The laser diodes 102 may comprise two laser diodes of the same wavelength, e.g. two 1470 nm laser diodes, or they may be different wavelengths, e.g. one 1470 nm laser diode and one 980 nm laser diode. In a currently preferred embodiment, the two laser diodes 102 have an output power of approximately 50 Watts each, for a combined power of approximately 100 Watts. Other wavelengths and combinations of wavelengths and power levels are also possible depending on the tissue effect that is desired from the surgical laser system 100. The aiming laser 104 is a low power laser source with a visible output beam. The aiming laser 104 may produce a single color aiming beam, e.g. red, yellow, green or blue, or it may produce multicolored aiming beams that may be continuous or may be modulated to indicate the operating status of the laser system, as described in the above-referenced patent applications.

The central component of the laser beam control and delivery system is an optical block 110 that has an input end 112, an output end 114, a right side 116 with a first connection port 118 and a left side 120, optionally having a second connection port 122. The optical block 110 is roughly the shape of a hollow rectangular solid with feet or flanges 124 having mounting holes 126 for mounting the optical block to an optical deck 130 or other support surface within the laser system. Other shapes are also possible. Preferably, the optical block 110 is machined from a single piece of aluminum or other metal for strength and stability.

Figure 10:
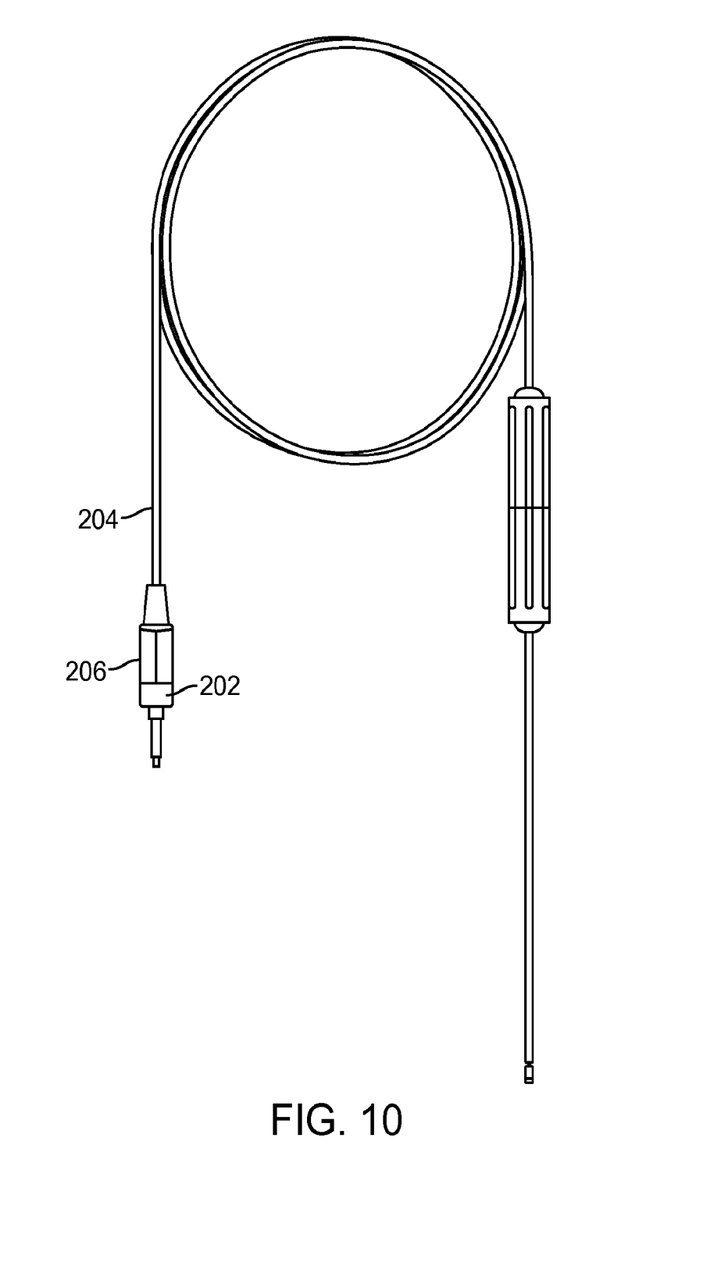
FIG. 10 illustrates an optical fiber device for use with the surgical laser system of the present invention.

The distal end of the beam combiner 106 is attached to an input port 132 on the input end 112 of the optical block 110. A collimating lens 134 is positioned to collimate the laser beam where it exits the distal end of the beam combiner 106 and enters the optical block 110. The input port 132 is aligned with an output port 146 on the output end 114 of the optical block 110. A refocusing lens 136 is positioned in front of the output port 146. Fine adjustment screws 138 are provided for adjusting the position of the output port 146 with respect to the input port 132 along X and Y axes. A connector 144 is provided on the output end 114 of the optical block 110 for insertion of the proximal end of an optical fiber 204 for delivering the laser beam to the surgical site, which is shown in FIG. 10. Optionally, the optical fiber 204 includes a proximal connector 206 that contains a device 202 for identifying the optical fiber 204 and recording data about the use of the optical fiber 204 and the surgical laser system 100. In one particularly preferred embodiment, the device 202 may be a 1-wire serial memory device. The proximal connector 206 may have electrical connections for communicating this information with the laser system or the proximal connector 206 may utilize radiofrequency identification (RFID) technology for one or two-way wireless communication with the laser system. In one preferred embodiment, an RFID tag placed on or near the proximal connector 206 of the optical fiber 204 communicates with a device on the surgical laser system using HF of near-field UHF transmission. No direct electrical connections are required.

A partially reflective mirror 140 or other type of beam splitter is positioned in the hollow space 128 of the optical block 110 between the input end 112 and the output end 114.

Preferably, the partially reflective mirror 140 is positioned at an angle of approximately 45 degrees with respect to an optical axis that extends from the input port 132 to the output port 146. Other mounting angles are also possible. The partially reflective mirror 140 is coated on both surfaces with an antireflective coating for the wavelength of the laser output beam(s) and coated on at least the distal, second surface with a reflective coating for infrared wavelengths.

The combined output beams from the two laser diodes and the aiming laser are emitted from the distal end of the beam combiner 106 and pass through the collimating lens 134 and the partially reflective mirror 140 and are focused on the proximal end of the optical fiber 204 by the refocusing lens 136 so that as much of the laser energy as possible passes into the core of the optical fiber 204. The optical fiber 204 is typically a 600 micron diameter fiber with a 550 micron diameter core. Other sizes of optical fibers can also be used.

Light returning to the output port 146 of the optical block 110 from distal portions of the optical fiber 204 strike the partially reflective mirror 140 and the infrared wavelengths and at least a portion of the visible wavelengths are reflected toward the first connection port 118 on the right side of the optical block 110. The first connection port 118 is typically between 10 and 1000 microns in diameter, most typically approximately 100 microns in diameter. A combined infrared detector and visible light detector 150 positioned at or optically connected to the first connection port 118 intercepts the reflected light and produces a first signal indicative of the magnitude of the returning infrared light that is used for temperature monitoring and control of the optical fiber 204 by the fiber tip protection system and a second signal indicative of the magnitude of the returning visible light that is used by the scope protection system and the fiber breakage detector, as described in the above-referenced patent applications. In some embodiments, the first and second signals and the ratio between them may be used for each of these functions.

Additional connection ports may be provided for additional sensors or other functions. An optical fiber, a hollow waveguide or holey fiber can be inserted into one or more of the connection ports to transmit the light to one or more sensors or detectors. Hollow waveguides will be particularly useful for transmitting light at higher wavelengths that are not readily transmitted through an optical fiber.

In an alternate embodiment, a partially reflective mirror 140 coated with a reflective coating for infrared wavelengths may be used to separate the returning infrared light from the returning visible light and direct them to separate detectors, as described in the above-referenced patent applications.

Sampling of the infrared signal by the fiber tip protection system will take place while the laser source is switched off briefly, e.g. for a few microseconds, so that the high intensity output beam of the laser will not overwhelm the signal from infrared light returning through the optical fiber 204. The signal-to-noise ratio of the infrared signal can be improved by using a phase-locked loop to eliminate other signals that are not in phase with the off periods of the laser source.

Figure 5:
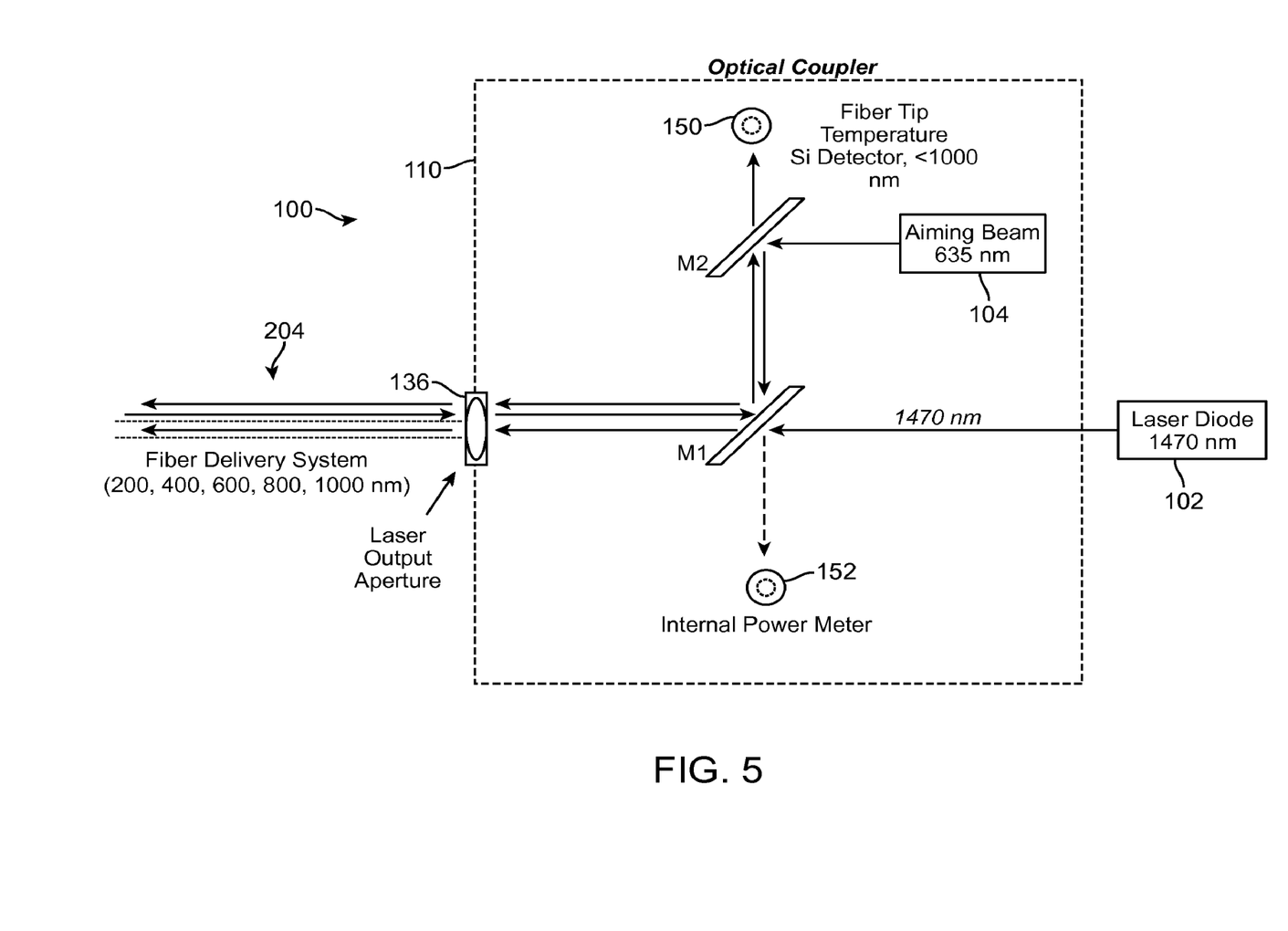
FIG. 5 is an optical diagram of a surgical laser system with fiber tip temperature sensing.

FIG. 5 is an optical diagram of a surgical laser system 100 that may utilize the laser beam control and delivery system of the present invention for fiber tip temperature sensing. This embodiment differs slightly from the embodiment illustrated in FIGS. 1 and 2 in that two partially reflective mirrors M1, M2 are used to combine the output of the laser diode 102 and the aiming beam laser 104 rather than the fiber optic beam combiner 106 described above. In this example, the laser diode 102 is a 1470 nm laser and the aiming beam laser 104 is a 635 nm, red laser. Mirror M1 is coated to transmit 1470 nm light and to reflect other wavelengths. Mirror M2 is coated to reflect 635 nm and "red" color and to transmit other wavelengths, including short IR wavelengths. In addition to the silicon IR and visible light detector 150 used for fiber tip temperature sensing, the surgical laser system 100 utilizes a second light detector 152 as an internal power meter. Most of the 1470 nm laser beam is transmitted directly through mirror M1, but a very small percentage of the beam is reflected toward the second light detector 152. The second light detector 152 will produce a signal that is proportional to the total energy of the 1470 nm laser beam, which can be used to provide a display of the actual laser energy produced and/or to compare the actual laser energy produced with the set power level to determine laser efficiency. This measure of laser efficiency can be used to schedule maintenance of the laser system.

Figure 3:
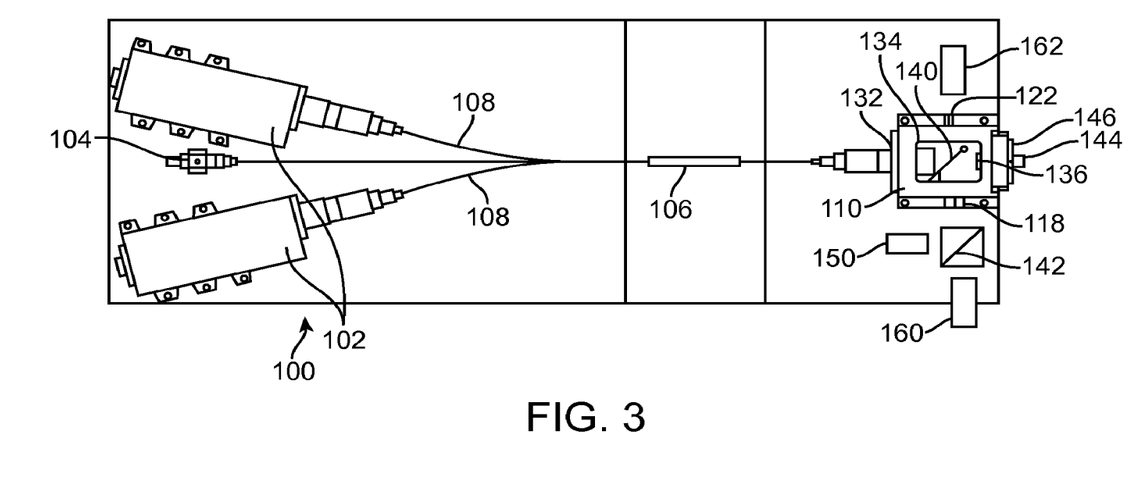
FIG. 3 shows an embodiment of the surgical laser system wherein the laser beam control and delivery system utilizes a camera for aligning the laser beam with the core of the optical fiber.

FIG. 3 shows an embodiment of the surgical laser system wherein the laser beam control and delivery system utilizes a camera 160 for aligning the laser beam with the core of the optical fiber 204. A small camera 160 such as a CMOS chip camera or CCD camera is mounted to intercept the reflected light from the partially reflective mirror 140 in the optical block 110. As shown in FIG. 3, a second partially reflective mirror 142 or other type of beam splitter coated with a reflective coating for infrared wavelengths may be used to separate the returning infrared light from the visible light. The second partially reflective mirror 142 directs the returning infrared light to an infrared detector 150, while the visible light is allowed to pass through to the camera 160. Alternatively, the second partially reflective mirror 142 may have a reflective coating for visible wavelengths to direct the visible light to the camera 160, while the infrared light is allowed to pass through to the infrared detector 150. The camera 160 provides an image of the proximal end of the optical fiber 204 allowing precise adjustment of the X and Y axes on the input port 132 so that the laser spot from the beam combiner 106 is positioned precisely on the core of the optical fiber 204 and not on the cladding or the jacket of the optical fiber. The camera 160 can also be used to image and identify any hotspots that develop when the laser is on. This will allow quick diagnosis and troubleshooting of problems with the optical fiber or alignment of the laser beam control and delivery system.

Alternatively, the camera 160 can be mounted directly to or optically connected to the first connection port 118 on the right side of the optical block 110. This can be done temporarily, for example to align the X and Y axes on the input port 132 during assembly of the laser system. A camera 160 can be permanently mounted directly to or optically connected to the first connection port 118 without the second partially reflective mirror 142 and without the infrared detector or visible light detector if the camera 160 is able to provide a quantitative measure of the returning infrared light and the returning visible light for use by the fiber tip protection system, the scope protection system and the fiber breakage detector.

In another embodiment of the surgical laser system, a second camera 162 can be mounted at or optically connected to the second connection port 122 on the left side of the optical block 110. The second camera 162 will produce an image of the input port 132 and surrounding structures. Information from the second camera 162 and/or an infrared detector may be used to determine the temperature and therefore the operating condition of the beam combiner 106, collimating lens 134, etc., which can be used to diagnose and troubleshoot problems with these parts of the laser beam control and delivery system. Since the partially reflective mirror has an antireflective coating for the laser wavelength, the camera will be safe from damage from the laser beam.

In another embodiment of the surgical laser system, the fiber tip protection system can be configured to provide a quantitative measure of the actual temperature of the fiber tip or other portions of the optical fiber. One means of accomplishing this is with two infrared detectors configured to sense infrared light in two different ranges of infrared wavelengths (or a single infrared detector capable of providing separate measures of infrared light in two different wavelength ranges). The total magnitude of the infrared signal will correlate with the location where the optical fiber is overheating (i.e. proximal end or distal end), whereas the ratio of the magnitudes of the signals in the two different ranges of infrared will correlate with the temperature of the hotspot detected. This infrared temperature sensor can be calibrated using a black body radiator (with emissivity of approximately 1) to create a look-up table to determine the temperature.

The thermal constant of the hotspot detected will also correlate with the location where the optical fiber is overheating and can be used for diagnosis and troubleshooting of problems with the optical fiber or alignment of the laser beam control and delivery system. For example, the infrared signal from carbonized tissue on the fiber tip will have a rapid decay, whereas the infrared signal from an overheated fiber tip will have a longer decay, and the infrared signal from an overheated optical block 110 will have a much longer decay time because of the higher thermal mass.

In another embodiment, the surgical laser system can be configured to provide a quantitative measure of the temperature of the target tissue. This capability would be useful in applications such as laser liposuction, wound healing, tissue welding and cancer detection. An infrared detector or camera for detecting short wavelength infrared (around 1.7 microns), such as an In/GaAs sensor, can be mounted in a manner similar to the visible light camera described above. Other types of infrared detectors that can be utilized include silicon, germanium and pyroelectric detectors. During periods that the laser source is switched off, the infrared detector or camera can detect the temperature of the target tissue. The infrared tissue temperature sensor can be calibrated using a black body radiator (with emissivity of approximately 1) to create a look-up table to determine the temperature.

For greater accuracy, a visible light camera can be used to produce a color image of the tissue being measured to estimate the emissivity of tissue. Charred tissue will have an emissivity of approximately 1, whereas normal tissue will have an emissivity of less than 1. A correction factor based on the estimated emissivity of the tissue can be applied to the infrared signal or a look-up table that takes both measures into account can be created.

Figure 6:
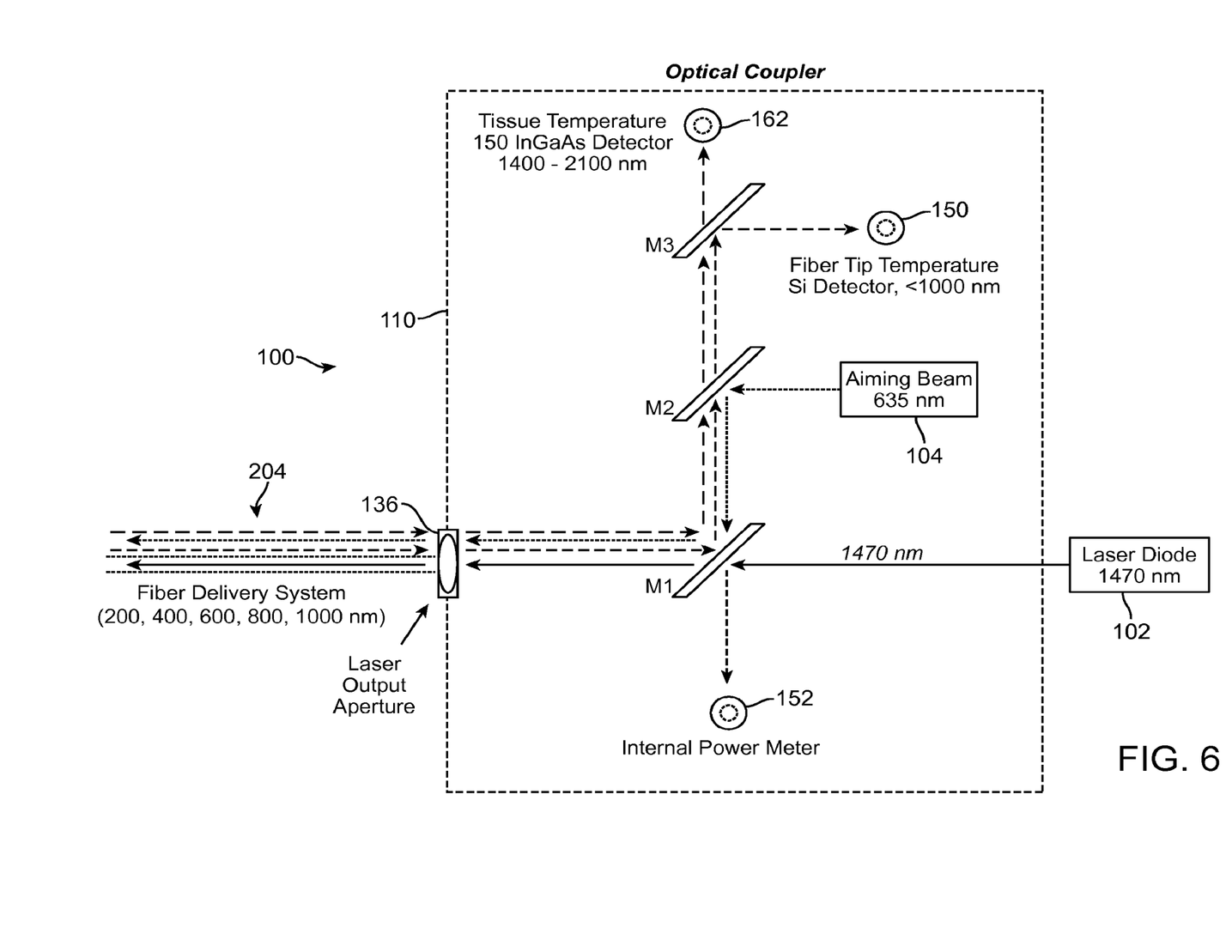
FIG. 6 is an optical diagram of a surgical laser system with fiber tip temperature sensing and tissue temperature sensing.

FIG. 6 is an optical diagram of a surgical laser system 100 that may utilize the laser beam control and delivery system of the present invention for fiber tip temperature sensing and tissue temperature sensing. This embodiment is similar to the embodiment illustrated in FIG. 5 except that it utilizes a third mirror M3 for separating the signals for fiber tip temperature sensing and tissue temperature sensing. Again, in this example, the laser diode 102 is a 1470 nm laser and the aiming beam laser 104 is a 635 nm, red laser. Mirror M1 is coated to transmit 1470 nm light and to reflect other wavelengths. Mirror M2 is coated to reflect 635 nm and "red" color and to transmit other wavelengths, including IR wavelengths. Mirror M3 is coated to reflect all wavelengths below 1000 nm, and to transmit light in the range of 1400 nm to 2100 nm wavelengths. Mirror M3 separates the light returning from the optical fiber 204 by reflecting the light below 1000 nm toward a silicon IR and visible light detector 150 for fiber tip temperature sensing and transmitting light in the range of 1400 nm to 2100 nm to an InGaAs infrared detector 162 for tissue temperature sensing. Most of the 1470 nm laser beam is transmitted directly through mirror M1, but a very small percentage of the beam is reflected toward the second light detector 152. The second light detector 152 will produce a signal that is proportional to the total energy of the 1470 nm laser beam, which can be used to provide a display of the actual laser energy produced and/or to compare the actual laser energy produced with the set power level to determine laser efficiency. This measure of laser efficiency can be used to schedule maintenance of the laser system. Alternatively, this embodiment laser system 100 may utilize a fiber optic beam combiner 106, as described above in connection with FIGS. 1 and 2, to combine the output beams of the laser diode 102 and the aiming beam laser 104.

The tissue temperature sensing may be calibrated using a black body radiator, as described above. Variations in the optical fiber 204 may affect the calibration of the tissue temperature sensing. To account for this, the transmission of each optical fiber 204 may be measure to determine a correction factor to be utilized by the laser system 100 for determining the tissue temperature. This correction factor may be entered manually by the operator, or the correction factor may be programmed into the memory device 202 in the proximal connector 206 of optical fiber 204 so that the laser system 100 will automatically recalibrate to the optical fiber 204 when it is plugged into the laser system 100.

Figure 4:
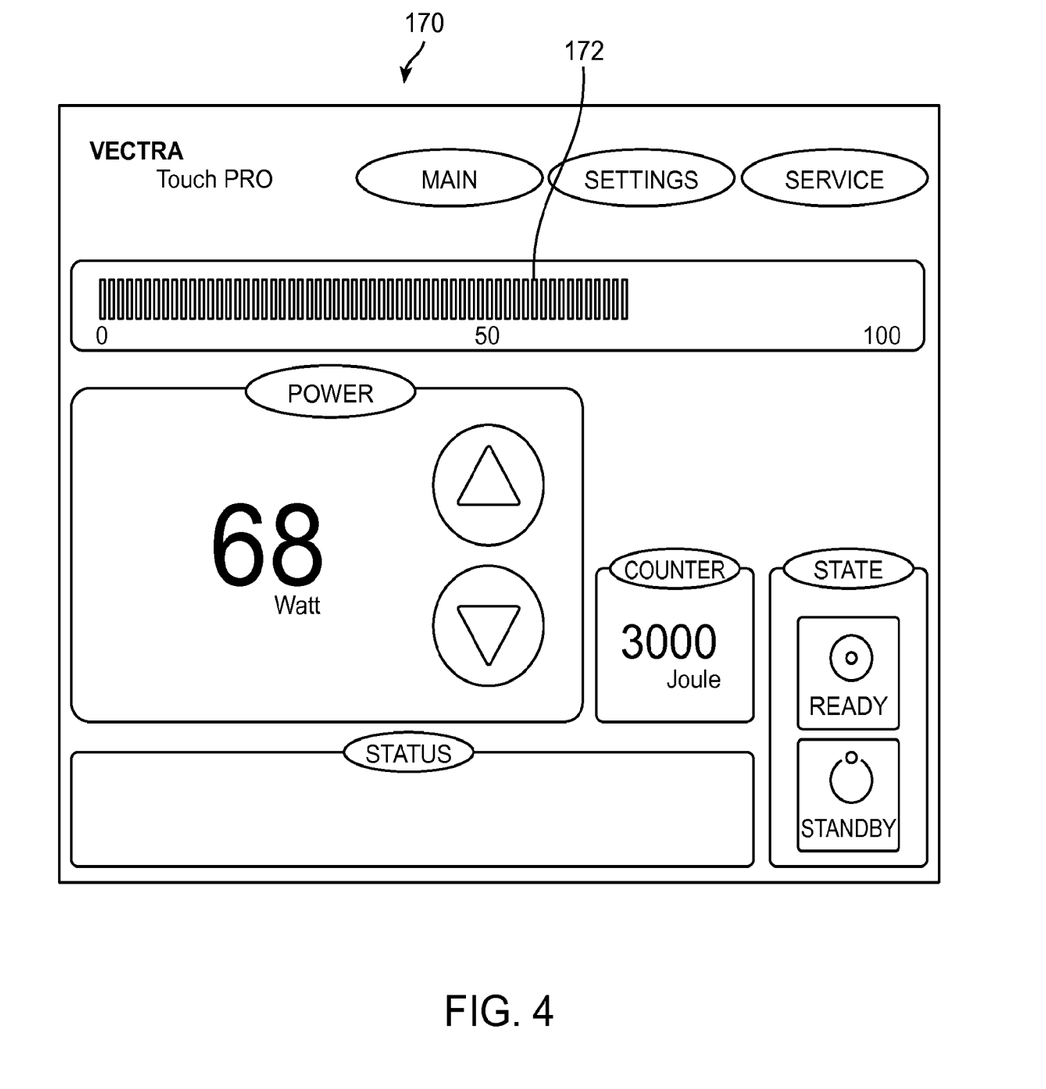
FIG. 4 illustrates the touch screen control panel of the surgical laser system.

FIG. 4 illustrates the touch screen control panel 170 of the surgical laser system. The touch screen control panel 170 includes a real-time bar graph 172 of the operating power of the laser diodes. The display may be in units of Watts of laser power, a percentage of the maximum power of the laser system or a percentage of the current laser power setting. This bar graph moves back and forth in real time to show the actual laser power being applied through the optical fiber by the laser control system. A reduction in the power level below the set power level is an indication that the fiber tip protection system has cut back on the laser power because the temperature of the fiber tip has reached its temperature threshold. In addition to the moving bar graph 172, the color of the bar graph can change to indicate the current operating condition of the optical fiber. For example, the bar graph can be green when the optical fiber is in good operating condition, it can turn yellow when the optical fiber is approaching the end of its usable life and it can turn red when the optical fiber has reached the end of its usable life and should be changed before continuing the surgical procedure. Other color schemes are, of course, possible. Alternatively or in addition, an optical fiber status indicator that changes color and/or size can be provided on the display panel separate from the power bar graph. Any one of these features will allow the operator to ascertain the current operating condition of the optical fiber with a quick glance at the display panel.

Figure 7:
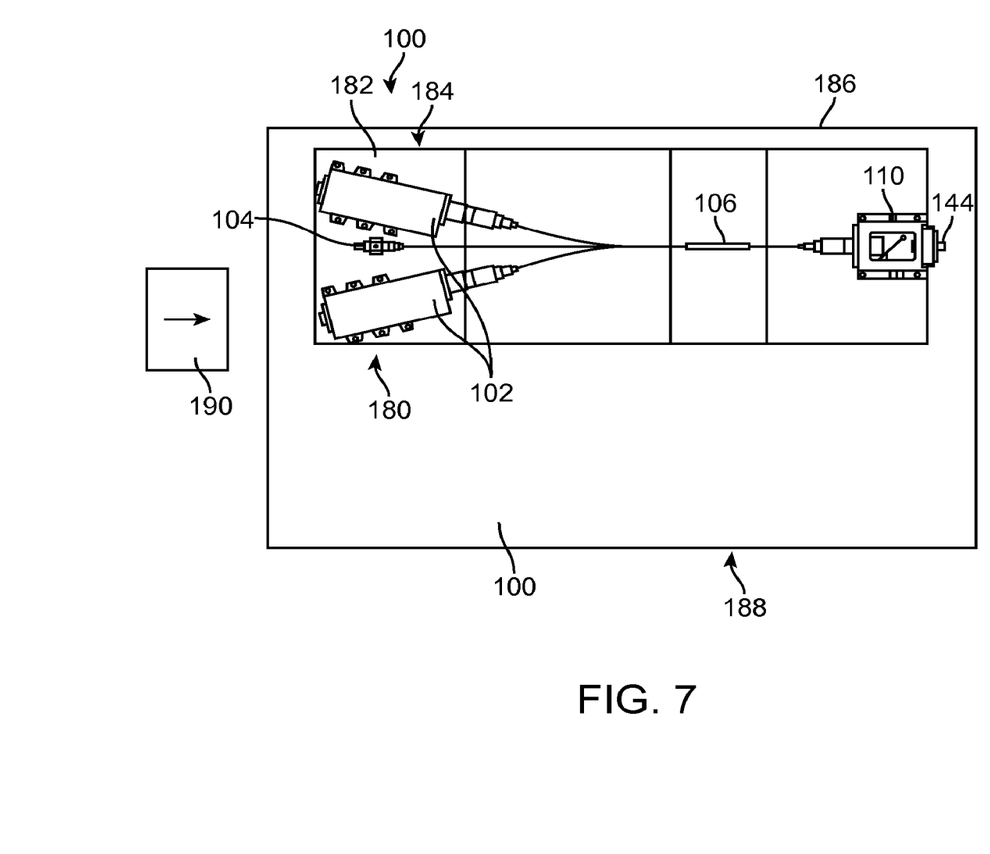
FIG. 7 is a plan view of a surgical laser system with a cooling system according to the present invention.
Figure 8:
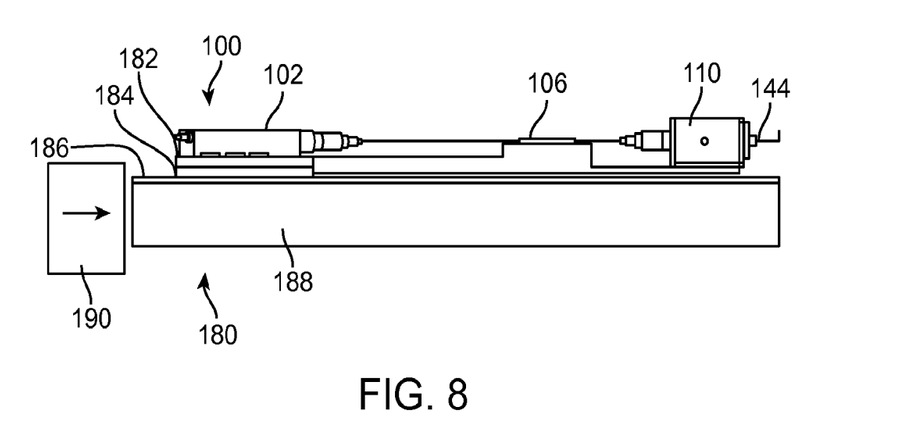
FIG. 8 is a side view of the surgical laser system and the cooling system of FIG. 7.

FIG. 7 illustrates a surgical laser system 100 that utilizes a cooling system 180 according to the present invention. FIG. 8 is a side view of the surgical laser system 100 and the cooling system 180 of FIG. 7. The surgical laser system 100 is preferably configured with a laser source that comprises one or more laser diodes 102. In the example shown, the surgical laser system utilizes two fiber-coupled laser diodes 102 and an aiming laser 104. The output beams from the two laser diodes 102 and the aiming laser 104 are combined using a beam combiner 106. The laser diodes 102 may comprise two laser diodes of the same wavelength, e.g. two 1470 nm laser diodes, or they may be different wavelengths, e.g. one 1470 nm laser diode and one 980 nm laser diode. In a currently preferred embodiment, the two laser diodes have an output power of approximately 50 Watts each, for a combined power of approximately 100 Watts. Other wavelengths and combinations of wavelengths and power levels are also possible depending on the tissue effect that is desired from the surgical laser system. The aiming laser 104 is a low power laser source with a visible output beam. The aiming laser may produce a single color aiming beam, e.g. red, yellow, green or blue, or it may produce multicolored aiming beams that may be continuous or may be modulated to indicate the operating status of the laser system, as described in the above-referenced patent applications.

The laser diodes 102 are highly efficient as compared to previous surgical laser systems that utilized gas lasers or solid state lasers, therefore the bulky, complicated and heavy fluid-circulating or refrigeration-cycle cooling systems that these other laser systems required are not needed. However, for stable operation of the laser diodes 102 some cooling system is still needed to maintain the laser diodes within their operating temperature range, particularly if the laser diodes are operated at high power for extended periods, as may be required in some surgical applications. The challenge is to create a cooling system that is compact, efficient and streamlined as befits the more compact and efficient laser diodes. Another challenge is to create a cooling system that is as quiet and free of vibration as possible. This attribute by itself would be a notable improvement over previous surgical laser systems.

Thermoelectric cooling uses the Peltier effect to create a heat flux between the junction of two different types of materials. A Peltier cooler or thermoelectric heat pump is a solid-state active heat pump which transfers heat from one side of the device to the other side against the temperature gradient (from cold to hot), with consumption of electrical energy. Thermoelectric coolers are available with cooling capacity sufficient for dissipating the waste heat produced by the laser diodes. However, the cooling ability of the thermoelectric cooler for this application is limited by the small surface area of the laser diode modules that is available for transferring heat to the cool side of the thermoelectric cooler. Directly coupling a thermoelectric cooler to the laser diode modules will not result in sufficient cooling to maintain the laser diodes within their operating temperature range because of the thermal resistance presented by the small thermal contact area of the laser diode modules. What is needed is a way to increase the effective thermal contact area of the laser diode modules for thermal coupling to a thermoelectric cooler in order to decrease the thermal resistance in the cooling system. The cooling ability of the thermoelectric cooler is also limited by the surface area on the hot side of the thermoelectric cooler that is available for dissipating heat. For this reason, it would also be advantageous to increase the effective surface area on the hot side of the thermoelectric cooler to further decrease the thermal resistance in the cooling system. It would be preferable to accomplish these objectives as efficiently as possible and without unduly increasing the bulk and complexity of the surgical laser system.

The cooling system of the present invention 180 utilizes a first heat spreader 182 to thermally couple the laser diodes 102 to the cool side of a thermoelectric cooler 184. The thermoelectric cooler 184 used in the currently preferred embodiment is capable of approximately 600 Watts of continuous cooling with a temperature difference from the hot side to the cool side of approximately 15 degrees Celsius, with a reserve power of approximately 900 Watts of cooling. Other sizes and power ratings of thermoelectric coolers may be appropriate for other laser systems. The first heat spreader 182 has an approximately planar configuration and simultaneously spreads the heat away from the laser diodes in two dimensions. This effectively increases the thermal contact area between the laser diode modules 102 and the cool side of the thermoelectric cooler 184. The materials and the structure of the first heat spreader are chosen to minimize the thermal resistance between the laser diode modules 102 and the cool side of the thermoelectric cooler 184. Preferably, the surface area of the first heat spreader 182 is approximately equal to the surface area of the cool side of the thermoelectric cooler 184, as additional surface area would be ineffective for heat transfer and therefore wasteful. In the example shown, the first heat spreader 182 has dimensions of approximately 156 by 120 mm, with a thickness of approximately 1-3 mm, and the thermoelectric cooler 184 has dimensions of approximately 156 by 120 mm, with a thickness of approximately 3-6 mm. Other dimensions for the first heat spreader 182 and the thermoelectric cooler 184 are also possible.

The cooling system utilizes a second heat spreader 186 to thermally couple the hot side of the thermoelectric cooler 184 to a heat sink 188 with cooling fins. The second heat spreader 186 has an approximately planar configuration and simultaneously spreads the heat away from the laser diodes in two dimensions. Configurations other than planar are also possible, particularly for the edges of the second heat spreader 186 that are beyond the edges of the thermoelectric cooler 184. The second heat spreader 186 increases the effective surface area on the hot side of the thermoelectric cooler 184 for decreased thermal resistance and improved heat dissipation. The materials and the structure of the second heat spreader 186 are chosen to minimize the thermal resistance between the hot side of the thermoelectric cooler 184 and the heat sink 188. Preferably, the second heat spreader 186 has a surface area that is significantly larger than the surface area of the hot side of the thermoelectric cooler 184. In the example shown, the second heat spreader 186 has dimensions of approximately 558 by 355 mm, with a thickness of approximately 1-3 mm, and the heat sink 188 has dimensions of approximately 558 by 355 mm, with cooling fins having a height of approximately 50 mm across the entire surface of the heat sink 188. Other dimensions for the second heat spreader 186 and the heat sink 188 are also possible. In this example, the thermoelectric cooler 184 has a surface area of approximately 19,800 mm squared and the second heat spreader 186 has a surface area of approximately 198,000 mm squared, or approximately ten times the surface area of the thermoelectric cooler 184. Other sizes and surface area ratios may be appropriate for use with other laser systems.

Preferably, the cooling system will also include one or more fans or blowers 190 for circulating cooling air across the cooling fins of the heat sink 188. For example, a high-performance variable speed electric fan, such as the Squall 50, available from Xcelaero Corp. of San Luis Obispo, Calif., may be used. The high efficiency of such a fan will reduce the overall power demands of the cooling system. Optionally, baffles or ducting may be used to direct and distribute the airflow from the fan 190 over the cooling fins of the heat sink 188.

In one embodiment of the cooling system of the present invention, the first and second heat spreader 182, 186 are configured as two-phase evaporative heat spreaders. One such heat spreader suitable for use in the present invention is the NanoSpreader™, which is commercially available from Celsia Technologies, Miami, Fla. The NanoSpreader™ is a copper encased two-phase vapor chamber into which pure water is vacuum sealed. The liquid is absorbed by a copper-mesh wick and passed as vapor through a micro-perforated copper sheet where it cools and returns as liquid to the wick. NanoSpreaders™ are half the weight of solid copper, yet can transfer heat at roughly ten times the rate (thermal conductivity). The NanoSpreader™ is a completely passive heat transfer device and requires no external power input. Multiple standard size or custom size NanoSpreader™ modules may be used together to achieve the dimensions of the heat spreaders noted in the example above. Other heat spreaders with different heat transfer fluids can also be used.

In one preferred embodiment, the second heat spreader 186 may be configured with cooling fins integrated directly into the two-phase evaporative heat spreader to act as an integral heat sink 188 and to reduce the number of material interfaces and therefore reduce the total thermal resistance of the cooling system.

In another embodiment of the cooling system of the present invention, the first and second heat spreader 182, 186 are constructed of a material with significantly higher thermal diffusivity and thermal conductivity than either aluminum or copper. One material suitable for use as heat spreaders in the present invention is CarbAl™, which is a carbon-based metal nanocomposite (CAI) comprised of 80% carbonaceous matrix and a dispersed metal component of 20% aluminum commercially available from Applied Nanotech Holdings, Inc., Austin, Tex. The nanocomposite heat spreader is a completely passive heat transfer device and requires no external power input. Another potential advantage of the nanocomposite heat spreader is that the heat transfer can be made directional. The nanocomposite heat spreader can be made to spread the heat in the X and Y directions and/or the Z direction to move the heat away from the diode laser modules as effectively as possible.

In one preferred embodiment, the second heat spreader 186 may be configured with the cooling fins integrated directly into the nanocomposite heat spreader to act as an integral heat sink 188 and to reduce the number of material interfaces and therefore reduce the total thermal resistance of the cooling system.

In other embodiments, the cooling system of the present invention may utilize a two-phase evaporative heat spreader for either the first or the second heat spreader 182, 186 and a nanocomposite heat spreader for the other heat spreader.

Another way to describe the configuration of the cooling system of the present invention is that the thermoelectric cooler 184, positioned with the cool side up and the hot side down, is "sandwiched" in between the first heat spreader 182 on the top and the second heat spreader 186 on the bottom. The laser diode modules 102 are mounted directly on top of the first heat spreader 182 for good thermal contact. The heat sink 188 with cooling fins is mounted directly below the second heat spreader 186 or, more preferably, integrated directly into the second heat spreader 186. Other orientations of the cooling system are also possible to accommodate different configurations of laser systems. Optionally, each interface of this "sandwich" can be configured to enhance thermal coupling between the various components. For example, contacting surfaces can be lapped together to improve surface-to-surface contact. Alternatively or in addition, thermal coupling can be enhanced by applying thermal grease or another heat transfer compound between contacting surfaces, by bonding with a thermally conductive adhesive or by soldering.

Preferably, the cooling system will include at least one temperature sensor for measuring the operating temperature of the laser diode modules. Optionally, additional temperature sensors may be used for measuring the temperature of the cool and/or hot side of the thermoelectric cooler 184 and/or the temperature of the heat sink 188. The signal(s) from the temperature sensor(s) will be used by a microcontroller for dynamic control of the cooling system. The microcontroller controls the current to the thermoelectric cooler 184 and, optionally, the current to the cooling fan(s) to maintain the operating temperature of the laser diode modules within an acceptable range. The microcontroller may use PID (proportional-integral-derivative) control, PWM (pulse width modulation) control or other known control scheme to optimize the power usage of the cooling system while maintaining the operating temperature of the laser diode modules within an acceptable range. One objective of the microcontroller is to optimize the heat exchange for the lowest possible power use. This helps to make the surgical laser system and cooling system capable of operating using a standard 120 volt AC outlet, without requiring more costly high amperage or 240 volt wiring in the operating room.

Optionally, the cooling system may be sealed into a thermally insulated box with a dry gas, such as dry nitrogen, inside to prevent condensation from forming on any of the cool side components. Only the heat sink 188 and the cooling fins would be exposed on the outside of the insulated box to allow the cooling air from the cooling fan(s) 190 to flow over the fins to dissipate heat. Alternatively, the cooling system may include a humidity sensor to avoid forming condensation on any of the cool side components. Moisture from condensation is not only potentially damaging to the components of the laser system and the cooling system, but it also indicates that the cooling system may be working too hard and wasting energy by condensing moisture from the air. Optimizing the power usage of the cooling system should include avoiding forming condensation.

If desired, the cooling system may be configured to transfer the waste heat farther away from the laser diode modules. For example, waste heat may be absorbed at the heat sink 188 and transferred to a heat exchanger located outside of the laser system enclosure. One technology for accomplishing this is a bubble pump closed loop liquid cooling system, such as the SILENTFLUX® bubble pump available from Noise Limit Inc., Cupertino, Calif. Another technology for accomplishing this is a loop heat pipe or a thermosyphon heat pipe, such as those available from Thermacore, Inc., Lancaster, Pa. These technologies are capable of transferring heat to a location from 1 to 23 meters from the heat source. They are passive devices that can operate silently. The only source of noise and vibration is the optional cooling fan that would be located at the heat exchanger.

Figure 9:
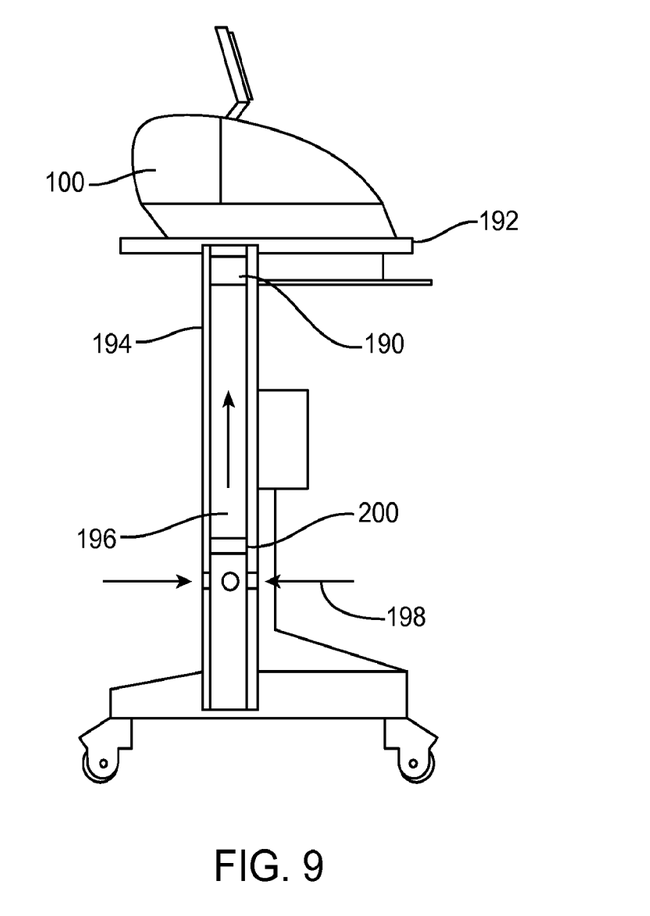
FIG. 9 illustrates a surgical laser system utilizing the support stand as part of the cooling system.

Another option would be to utilize the support stand 192 for the laser system 100 as part of the cooling system. FIG. 9 illustrates a surgical laser system 100 utilizing the support stand 192 as part of the cooling system. Various components of the cooling system could be housed in the support stand, such as the cooling fan 190 and/or an external heat exchanger. Locating an external heat exchanger in the support stand 192 connected to the cooling system 180 would move waste heat farther from the source of heat at the diode laser modules. This arrangement could also reduce the total noise level of the laser system 100. In one option, the pedestal leg 194 of the support stand 192 could be used as an air duct 196 to bring cool air up underneath the laser system enclosure. As shown in FIG. 9, a cooling fan 190 could bring cool air in through side holes 198 located on the pedestal leg 194 of the support stand above the floor level. A screen and/or filter 200 can be used to prevent the cooling fan from bringing in dust or debris.

Although the cooling system of the present invention has been described in connection with a diode laser system, the cooling system may also be used for temperature management in other laser systems, such as gas lasers or solid state lasers, or in other electronics or industrial applications requiring a cooling system.

While the present invention has been described herein with respect to the exemplary embodiments and the best mode for practicing the invention, it will be apparent to one of ordinary skill in the art that many modifications, improvements, combinations and subcombinations of the various embodiments, adaptations and variations can be made to the invention without departing from the spirit and scope thereof.

The invention claimed is:

1. A laser system comprising:
a first laser module emitting a first laser beam at a first wavelength;
a partially reflective first mirror positioned in a path of the laser beam, the partially reflective first mirror being transmissive for the first wavelength and coated on a distal surface with a first reflective coating for infrared wavelengths of light, said partially reflective first mirror further having more than a single non-reflective coating;
an optical fiber positioned in the path of the laser beam distal to the partially reflective first mirror;
the partially reflective first mirror being positioned such that the first reflective coating reflects a beam of infrared light returning from the optical fiber onto a partially reflective second mirror, the partially reflective second mirror being transmissive for infrared light with a wavelength in the range of 1400 to 2100 nm and coated on a first surface with a second reflective coating for wavelengths of light below 1000 nm;
a first light detector sensitive to light with a wavelength below 1000 nm positioned to intercept light reflected from the partially reflective second mirror;
and a second light detector sensitive to infrared light with a wavelength in the range of 1400 to 2100 nm positioned to intercept light passing through the partially reflective second mirror.

2. The laser system of claim 1,
wherein the partially reflective first mirror is coated on at least one surface with a nonreflective coating for the first wavelength.

3. The laser system of claim 1, further comprising:
an aiming laser emitting a laser beam at a visible wavelength; and
a partially reflective third mirror positioned between the partially reflective first mirror and the partially reflective second mirror, the partially reflective third mirror being coated on at least one surface with a third reflective coating for the visible wavelength and transmissive for other wavelengths of light.

4. The laser system of claim 3,
wherein the visible wavelength is 635 nm.

5. The laser system of claim 1, further comprising:
a third light detector sensitive to the first wavelength, the third light detector positioned to intercept a portion of the first laser beam reflected from the partially reflective first mirror.

6. The laser system of claim 1,
wherein the first wavelength is 1470 nm.

7. The laser system of claim 1, further comprising:
a second laser module emitting a second laser beam at a second wavelength; and
means for combining the first laser beam and the second laser beam.

8. The laser system of claim 7,
wherein the first laser module and the second laser module are fiber-coupled laser diodes, and
wherein the means for combining the first laser beam and the second laser beam comprises a fiber optic beam combiner.

9. A laser system comprising:
a first laser module emitting a first laser beam at a first wavelength;
a first mirror positioned in a path of the laser beam,
wherein the first mirror is configured to be transmissive for the first wavelength,
wherein the first mirror is coated on at least one surface with a first reflective coating for infrared wavelengths of light;
a second mirror,
wherein the second mirror is configured to be transmissive for infrared light with a wavelength in the range of 1400 to 2100 nm,
wherein the second mirror is coated on at least one surface with a second reflective coating for wavelengths of light below 1000 nm;
an optical fiber positioned in the path of the laser beam,
wherein the first mirror is positioned such that the first reflective coating reflects a beam of infrared light returning from the optical fiber onto the second mirror;
a first light detector sensitive to light with a wavelength below 1000 nm positioned to intercept light reflected from the second mirror; and
a second light detector sensitive to infrared light with a wavelength in the range of 1400 to 2100 nm positioned to intercept light passing through the second mirror.

10. A laser system comprising:
a first laser module emitting a first laser beam at a first wavelength;
a first mirror positioned in a path of the laser beam,
wherein the first mirror is configured to be transmissive for the first wavelength,
wherein the first mirror is coated on at least one surface with a first reflective coating for infrared wavelengths of light;
a second mirror,
wherein the second mirror is configured to be transmissive for infrared light with a wavelength in the range of 1400 to 2100 nm,
wherein the second mirror is coated on at least one surface with a second reflective coating for wavelengths of light below 1000 nm;
an optical fiber positioned in the path of the laser beam,
wherein the first mirror is positioned such that the first reflective coating reflects a beam of infrared light returning from the optical fiber onto the second mirror;

a first light detector sensitive to light with a wavelength below 1000 nm positioned to intercept light reflected from the second mirror;
a second light detector sensitive to infrared light with a wavelength in the range of 1400 to 2100 nm positioned to intercept light passing through the second mirror;
an aiming laser emitting a laser beam at a visible wavelength; and
a third mirror positioned between the first mirror and the second mirror,
  wherein the third mirror is coated on at least one surface with a third reflective coating for the visible wavelength,
  wherein the third mirror is configured to be transmissive for other wavelengths of light.

* * * * *